(12) United States Patent
Bunce et al.

(10) Patent No.: US 7,871,237 B2
(45) Date of Patent: Jan. 18, 2011

(54) METHOD AND APPARATUS FOR MONITORING PARTICLES IN A GAS TURBINE WORKING FLUID

(75) Inventors: Richard H. Bunce, Altamonte Springs, FL (US); Francisco Dovali-Solis, Oviedo, FL (US)

(73) Assignee: Siemens Energy, Inc., Orlando, FL (US)

(*) Notice: Subject to any disclaimer, the term of this patent is extended or adjusted under 35 U.S.C. 154(b) by 1229 days.

(21) Appl. No.: 11/482,614

(22) Filed: Jul. 7, 2006

(65) Prior Publication Data

US 2008/0016971 A1 Jan. 24, 2008

(51) Int. Cl.
*F01D 21/00* (2006.01)
*F01D 21/10* (2006.01)
*F01D 21/12* (2006.01)
*F01D 21/14* (2006.01)

(52) U.S. Cl. .................. 415/1; 415/13; 415/17; 415/26; 415/47; 415/116; 340/606; 340/609; 340/611; 340/612; 340/603; 702/24; 702/26; 702/27; 702/29; 702/30; 702/31; 702/32; 702/46; 702/50; 702/114; 702/127; 702/128; 702/182; 702/183; 702/187; 702/189; 73/23.33

(58) Field of Classification Search .............. 415/1, 415/13, 17, 26, 28, 47, 115, 116; 416/61, 416/95, 96 R, 96 A, 97 R; 340/603–623; 702/26, 29, 27, 30–32, 22–24, 45–46, 50, 702/114, 127–128, 182–183, 187, 189; 73/23.33
See application file for complete search history.

(56) References Cited

U.S. PATENT DOCUMENTS

| | | | |
|---|---|---|---|
| 2,739,302 A * | 3/1956 | Timbie | 340/611 |
| 3,993,017 A | 11/1976 | De brey | |
| 4,015,135 A | 3/1977 | Tipton, Jr. | |
| 4,080,535 A | 3/1978 | Phillips et al. | |
| 4,135,246 A | 1/1979 | McMannis | |
| 4,160,908 A | 7/1979 | Phillips | |
| 4,296,628 A | 10/1981 | Mast | |
| 5,070,722 A | 12/1991 | Hawman et al. | |

(Continued)

OTHER PUBLICATIONS

"On-line Particle Sizers" "Achieving your process vision", ref: MRK397-01; [online]; [unknown retrieval date];8 pages; Retrieved from http://www.malvern.co.uk/common/downloads/Malvern_Process_Systems_Brochure_2002.pdf; Malvern Instruments, Ltd, Malvern, Worcestershire, United Kingdom.

*Primary Examiner*—Christopher Verdier

(57) ABSTRACT

A method and system for monitoring a gas turbine engine (20) to predict maintenance requirements. Particles suspended in a gas flow (24, 32) of the engine (20) are monitored and quantified to predict a particle accumulation rate. Monitoring may be done using particle flow sensors (61-63) in a diverted portion (33) of the working gas flow (24), such as in the cooling gas flow (32). Particle sampling (S1-S3) may be done to determine particle size and composition distributions. Particle mass flow rates may then be continuously monitored per engine operating condition, and compared to predetermined values such as a normal upper limit per engine operating condition. An integrated particle mass flow may be used in conjunction with an instantaneous mass flow rate to predict a maintenance requirement. Multiple locations (L1-L3) may be monitored to recognize a maintenance requirement by flow section or component.

15 Claims, 2 Drawing Sheets

U.S. PATENT DOCUMENTS

| | | |
|---|---|---|
| 5,185,997 A | 2/1993 | Nishijima |
| 5,196,170 A | 3/1993 | Patashnick et al. |
| 5,552,711 A * | 9/1996 | Deegan et al. ............... 415/118 |
| 5,822,883 A | 10/1998 | Horwitz |
| 5,918,458 A | 7/1999 | Coffinberry et al. |
| 5,932,795 A | 8/1999 | Koutrakis et al. |
| 6,062,811 A * | 5/2000 | Zombo et al. ............... 415/118 |
| 6,413,044 B1 | 7/2002 | Roeloffs et al. |
| 6,427,448 B1 * | 8/2002 | Reichert ..................... 415/115 |
| 6,668,655 B2 | 12/2003 | Harrold et al. |
| 6,829,919 B2 | 12/2004 | Sioutas et al. |
| 6,971,258 B2 | 12/2005 | Rhodes et al. |
| 2005/0068527 A1 | 3/2005 | Nuspliger |
| 2005/0217351 A1 * | 10/2005 | Kreck et al. .................. 702/31 |

* cited by examiner

METHOD AND APPARATUS FOR MONITORING PARTICLES IN A GAS TURBINE WORKING FLUID

FIELD OF THE INVENTION

The invention relates to continuous monitoring of contaminant particles suspended in a gas flow in a gas turbine engine to recognize and predict maintenance requirements for components of the gas turbine and cooling system.

BACKGROUND OF THE INVENTION

Gas turbine engines use an air compressor to provide a working fluid flow for combustion and power cycles. A portion of this working flow may be diverted into a cooling system to provide cooling air for turbine blades and vanes. Cooling air may be routed through a heat exchanger, then channeled through the interior of each blade and vane airfoil, and finally discharged from small holes in these airfoils into the turbine air stream to draw heat away from the surfaces of the airfoils. Cooling allows the use of high engine operating temperatures that would otherwise be detrimental to the structural integrity of the blades and vanes.

An unintended consequence of this removal and return of cooling air from the turbine system is that solid particle matter is entrained in the cooling air stream. Particles may become suspended in the cooling air by ingestion in the inlet air and by entrainment of corrosion from surfaces exposed to the air. Filters are used to remove larger particles from the cooling air flow.

BRIEF DESCRIPTION OF THE DRAWINGS

The invention is explained in following description in view of the drawings that show.

DETAILED DESCRIPTION OF THE INVENTION

Contaminant particles entrained in the cooling air of a gas turbine engine can accumulate on surfaces in the cooling air piping and channels. The inventors have recognized that such accumulations can increase maintenance costs and reduce the availability of the engine. The inventors further recognized that the cooling air is representative of the gas turbine working fluid flow at the point of cooling air extraction, and that it contains particles ingested from the environment and those entrained from internal corrosion in the compressor and the cooling system. Predicting particle accumulations using analytical methods alone has been unsatisfactory, because particle concentrations depend upon a variety of unpredictable factors such as changes in environmental conditions. Such factors can cause unexpected acceleration of corrosion or ingestion of particles. The inventors recognized that continuously monitoring particles in the cooling air could offer significant improvements in efficiency and safety of engine operation, allowing early detection of increased particle flow from any cause and facilitating a predictive capability that provides for safe, efficient operation and for condition-based maintenance.

Figure 1:
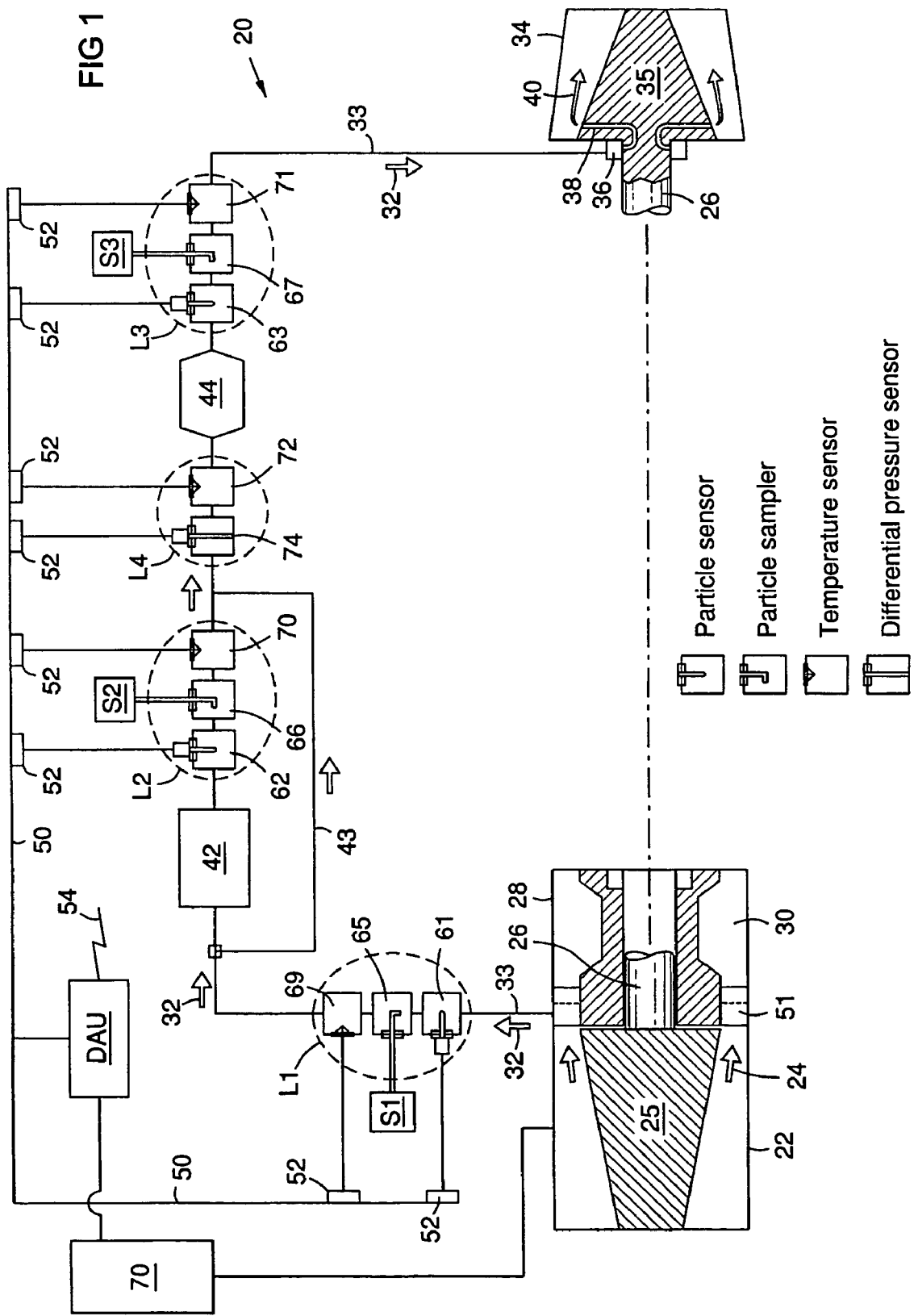
FIG. 1 is schematic illustration of a particle monitoring system in a gas turbine engine according to an aspect of the invention.

FIG. 1 schematically illustrates a gas turbine engine 20, having a compressor section 22 with a compressor rotor 25 driven by a rotating shaft 26 to produce compressed air 24 as a working fluid flow for combustion and cooling. A combustion section 28 has one or more combustors 30. A compressed air plenum 51 supplies compressed air 24 to the combustors 30, and may include a diffuser that slows the air flow to convert some dynamic pressure to static pressure. A turbine section 34 has a turbine rotor 35 with aerodynamic blades that are driven by hot combustion gases from the combustors 30. This drives the shaft 26, which drives the compressor rotor 25. In power generation applications, an extension of the shaft 26 may drive an electric generator (not shown). Alternately, a second downstream turbine section (not shown) may drive a generator. A portion 32 of the compressed air 24 is diverted from the working fluid flow for cooling purposes via piping 33. A heat exchanger 42 may cool the cooling air 32, and a filter 44 may remove suspended particles from it. A bypass line 43 around the heat exchanger may provide control of the cooling air temperature. A cooling air injector 36 may surround part of the shaft 26 and inject cooling air 32 into channels 38 in the shaft 26 that route the cooling air 32 through the turbine rotor 35 and blades. Other components (not shown) of the engine, such as the combustor and the stationary vanes, may be cooled by the cooling air. The cooling air 32 may exit small holes in the blades, and pass into the working fluid and to the turbine exhaust as indicated at arrows 40. An engine control system 70 is electronically connected to sensors, controllers, operator terminals, and actuators that monitor and control the engine operations as known in the art.

To monitor particles suspended in the cooling air flow 32, one or more particle sensors 61-63 may be mounted at one or more location(s) L1-L3 in the cooling piping 33. An example of such a sensor is the PCME® DT990 electrodynamic sensor, which senses passing particles by detecting their electrostatic charge. The antenna of this sensor may be custom engineered to withstand the temperature and dynamic pressure of the cooling air flow 32. The particle sensors 61-63 provide particle flow data via a data bus 50 and interface circuits 52 to a data acquisition unit DAU. The particle flow data may be in units such as particle counts or particle mass density.

To convert such particle flow data to particle mass flow values, the particles may be sampled and analyzed to determine their composition and size distributions. This may be done by installing particle sampling devices 65-67 at one or more locations L1-L3 of the respective particle sensor(s) 61-63 or at other locations. The sampling devices 65-67 may have collection probes in the piping 33. The probes may be tubes or channels with isokinetic tips or openings as known in the art for diverting a portion of the cooling air to a filter, such as thimble filters S1-S3 for example. A needle valve and a differential pressure gauge across each thimble filter S1-S3 may be used to set an air flow rate through the thimble filter. This differential pressure configuration or other configurations known in the art may be used for monitoring the condition of the filter. Each thimble filter S1-S3 collects particles from the cooling air stream. Tubing upstream of the filter will be relatively hot, and may be made of heat resistant material such as Inconel® 600 to minimize oxidation inside the sampling tubing. Other tubing may be made of less expensive material, such as stainless steel. The thimble filters may be changed periodically when the differential pressure gage indicates that a significant amount of particle matter has collected. The filters S1-S3 collect samples of the particles for analysis by a laboratory. Samples may be taken under each of several stages of engine operation.

Alternate sampling strategies may be used. For example, particle sampling and analysis may be done in a given engine, and the resulting particle size and composition data may be used to calibrate particle mass flow measurements in other engines of the same type. In another strategy, a continuous particle size distribution sensor may be installed in the piping based on laser diffraction or other known techniques.

A differential pressure sensor 74 may be mounted in the piping 33. This may include a Pitot device that senses dynamic pressure and static pressure of the cooling air flow 32, and calculates a flow velocity from these measurements. It may also include a temperature sensor 72 to derive density and mass flow measurements of the cooling air flow 32. An example of this type of sensor is a Rosemount® integrated Annubar® system.

A data acquisition unit DAU collects data from the various sensors 61-63, 65-67, 69-72, and 74 of the invention via one or more electronic data buses 50. Interface circuits 52 may be provided on the buses and/or in the sensors to condition electronic signals from the sensors for communication with the data acquisition unit. The data acquisition unit DAU compiles and stores data for analysis and inquiry. It may have a data communications link 54 for off-site monitoring and analysis of the sensor data. The data acquisition unit DAU may include a processing capability and algorithms for computing derived parameters from the sensor data. Alternately, one or more of the sensors 61-63, 65-67, 69-72, and 74 may include electronics that compute some or all derived parameters.

Figure 2:
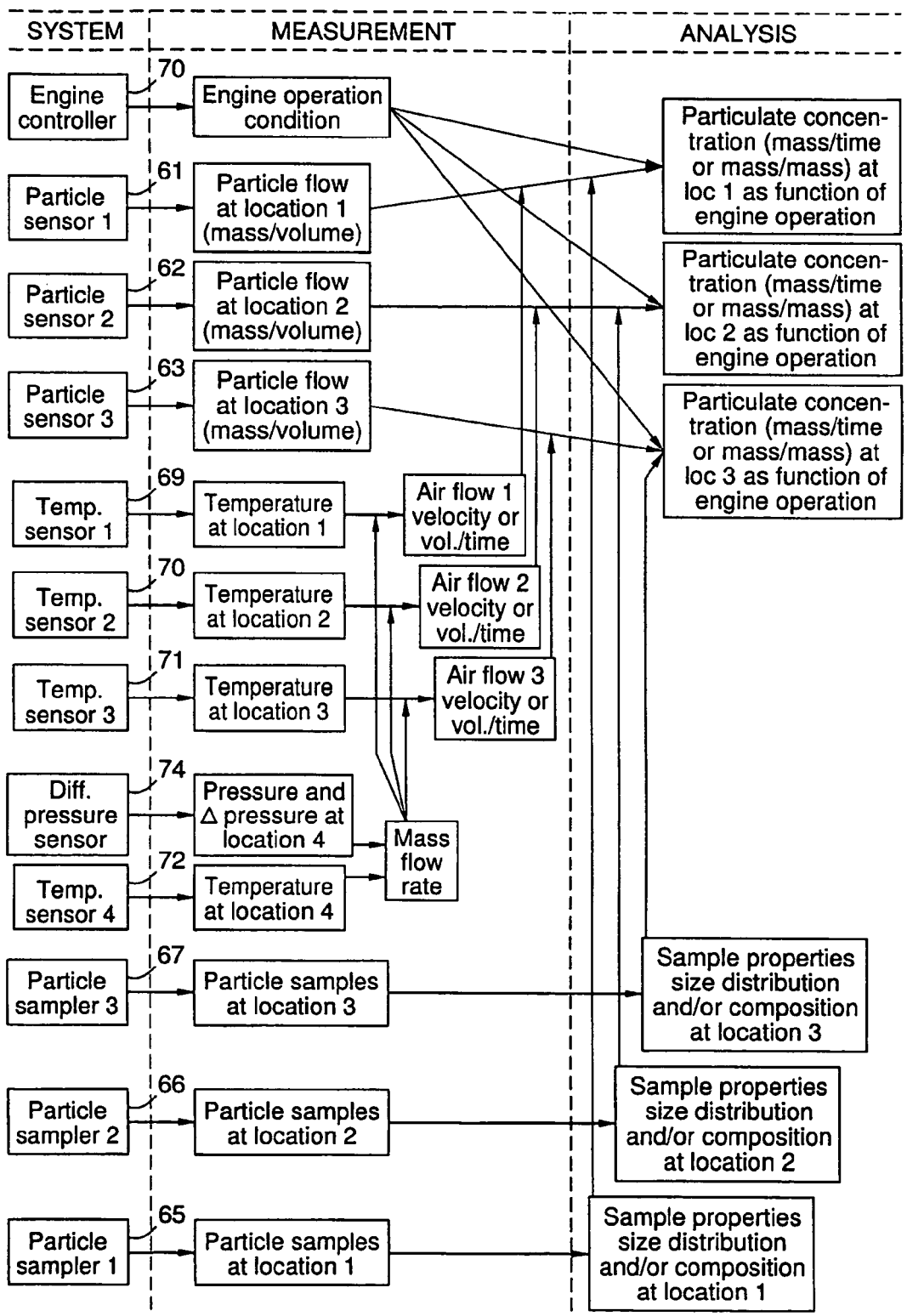
FIG. 2 is a function chart of elements, measurements, and analysis in a gas turbine engine according to an aspect of the invention.

FIG. 2 is a function diagram 80 showing elements of the monitoring system, measurements returned by these elements, and analyses in an example embodiment. Parts of this diagram may vary depending on the number of monitoring locations, the specific sensors used, and the parameters to be used for analysis. For example, a particle sensor 61-63 may return a particle count N or it may return a particle density ($mg/m^3$) using a previous calibration. Analysis steps may use a particle mass flow rate, an integrated particle mass flow since a given time, a particle mass density per cooling air volume and/or other parameters. Parameters not provided directly by the sensors can be derived from the sensor data using known formulas of fluid dynamics.

Analysis may include comparing a parameter such as an instantaneous particle mass flow rate to a predetermined value such as a normal upper limit of particle mass flow rates for a given engine operating condition. Analysis may further include determining a maintenance requirement as a function of an integrated particle mass flow, with or without consideration of an instantaneous particle mass flow. If multiple locations are monitored, the parameters may be compiled in a matrix with a cell for each parameter per location per engine operating condition. The data and analyses may be consolidated into reports and graphs by section being monitored. These presentations may highlight exceptions such as accelerated corrosion. Analyses may be done by algorithms in the data access unit DAU or in an attached on-site computer, or they may be done remotely using a remote client computer via such algorithms and/or graphical displays for interactive operator analysis.

The present invention contemplates real time measurement of particle flow information during various phases of operation of a gas turbine engine. In a diagnostic mode, the invention may include the installation of an on-line particle detection system effective to provide a particle flow value associated with a portion of the working fluid flowing through a gas turbine engine, such as the portion diverted for cooling flow purposes. Particle flow information is then collected and analyzed for various modes of operation of the engine. Grab samples of the particles are collected as necessary to calibrate and characterize the on-line particle flow value information. Data may be collected from various locations in the fluid flow path, thereby facilitating an analysis of the various sources of particles. Similar data may be collected on a plurality of engines and statistics may be generated to represent a fleet of engines. In a monitoring mode, on-line particle data may be compared to predetermined set points for the generation of alarms for the engine operator and for the recognition of an action, such as adjusting an operating parameter of the engine, shutting down the engine, or performing a maintenance activity on the engine, for examples. Such set points may vary in response to an operating condition of the engine, such as having a higher expected particle flow rate during startup after the plant has been idle for a period of time. Such set points may also be varied as a function of an integrated value of the particle flow, such as lowering an alarm, maintenance or shutdown value as the total mass flow of particles accumulates over time. Particle flow information integrated over time may be used to predict a need for a maintenance service, such as cleaning of cooling flow passages or other surfaces, in order to prevent particle-induced changes in the engine performance. For example, the prediction of an engine shutdown date for a cleaning activity may be responsive to an instantaneous value of the particle flow rate. Changes in particle flow values may be correlated to other engine operating conditions for diagnosis and maintenance decisions. Plant design decisions may reflect the availability of such on-line particle flow information. For example, because actual, real-time particle flow data is available, a decision may be made to construct at least a portion of a cooling air system with less-expensive carbon steels that are more subject to corrosion and the generation of particles than the alternative more-expensive stainless steels or internally coated materials. Alternatively, a decision may be made to invest in corrosion-resistant materials for other portions of a plant, such as the compressor casing for example.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A method comprising:
   disposing a solid particle detection sensor in a working fluid flow of a gas turbine engine;
   communicating data from the solid particle detection sensor to a processor;
   using the processor to perform the following steps;
   continuously obtaining flow values of solid particles from the working fluid flow;
   comparing the solid particle flow values to a predetermined upper limit for a given engine operating condition;
   recognizing a required action in response to the comparison; and
   continuously obtaining the solid particle flow value values from a cooling fluid flow diverted from a compressor of the gas turbine engine;
   continuously sensing solid particle flow values at a plurality of locations along the cooling fluid flow; and
   diagnosing a location of a source of solid particles by evaluating the respective solid particle flow values.

2. The method of claim 1 further comprising:
   integrating solid particle flow values over time;

comparing the integrated solid particle flow values to a predetermined integrated value.

3. The method of claim 2 further comprising undertaking a maintenance activity in response to the integrated solid particle flow values.

4. The method of claim 2 wherein the predetermined upper limit is a solid particle mass upper limit and wherein the integrated solid particle flow values are derived from a measured solid particle flow count and established solid particle size and composition distributions.

5. The method of claim 4, wherein the solid particle size and composition distributions are established by analyzing samples of solid particles taken from the working fluid flow.

6. The method of claim 4, further comprising lowering the predetermined upper limit as a total mass flow of solid particles accumulates over time.

7. A method comprising:
disposing a solid particle detection sensor in a cooling fluid flow of a gas turbine engine;
communicating data from the solid particle detection sensor to a processor;
using the processor to perform the following steps;
monitoring a flow value of solid particles comprising ingested particles in the cooling fluid flow of the gas turbine engine; and
recognizing a required action for the gas turbine engine in response to the solid particle flow value in comparison to a predetermined upper limit that varies as a function of an operating condition of the gas turbine engine; and
changing the predetermined upper limit as a function of an integrated value of the solid particle flow value.

8. The method of claim 7, further comprising undertaking the action when the integrated value of the solid particle flow value exceeds the predetermined upper limit.

9. The method of claim 7, further comprising predicting the action as a function of an instantaneous value of the solid particle flow value as the integrated value of the solid particle flow value approaches the predetermined upper limit.

10. The method of claim 7 wherein the cooling fluid flow is a flow diverted from a plenum between a compressor and a combustor of the gas turbine engine.

11. A gas turbine engine comprising:
an air compressor that produces a cooling fluid flow;
a cooling system that diverts a portion of the cooling fluid flow through piping:
a solid particle sensor mounted in the piping for sensing solid particles suspended in the diverted portion of the cooling fluid flow;
a data acquisition system that receives real-time data from the solid particle sensor during a plurality of engine operating conditions; and
a processor that compares the real-time data to an upper limit that varies as a function of the engine operating conditions and recognizes a required action resulting from the comparison.

12. The gas turbine engine of claim 11, further comprising a device mounted in the piping for determining a size distribution of the suspended solid particles.

13. The gas turbine ending of claim 12, wherein the upper limit is lowered as a total mass flow of the suspended solid particles accumulates over time.

14. The gas turbine ending of claim 13, wherein the upper limit is increased during a startup condition of the engine.

15. The gas turbine engine of claim 11, further comprising a device mounted in the piping for extracting a sample of the suspended solid particles.

* * * * *